United States Patent [19]

Waldvogel

[11] 4,107,434
[45] Aug. 15, 1978

[54] PROCESS FOR MAKING PLEUROMUTILINS

[75] Inventor: Erwin Waldvogel, Convent Station, N.J.

[73] Assignee: Sandoz Ltd., Basel, Switzerland

[21] Appl. No.: 757,858

[22] Filed: Jan. 10, 1977

[30] Foreign Application Priority Data

Jan. 15, 1976 [CH] Switzerland ............... 450/76

[51] Int. Cl.² .................................... C07D 295/14
[52] U.S. Cl. ........................... 544/59; 544/107; 544/158; 544/380; 260/268 TR; 560/153; 424/246

[58] Field of Search .......... 260/481 R, 247.1, 268 PC, 260/268 TR, 243 B; 560/153; 540/107; 544/158, 59

[56] References Cited

U.S. PATENT DOCUMENTS

| 3,919,290 | 11/1975 | Egger et al. ............... 260/481 R |
| 3,972,887 | 8/1976 | Freedman ..................... 260/973 |

*Primary Examiner*—Jose Tovar
*Attorney, Agent, or Firm*—Gerald D. Sharkin; Robert S. Honor; Thomas O. McGovern

[57] ABSTRACT

Novel process for the production of antibacterially active pleuromutilin derivatives.

7 Claims, No Drawings

PROCESS FOR MAKING PLEUROMUTILINS

This invention concerns pleuromutilin derivatives.

More particularly, this invention provides a process for the production of compounds of formula I,

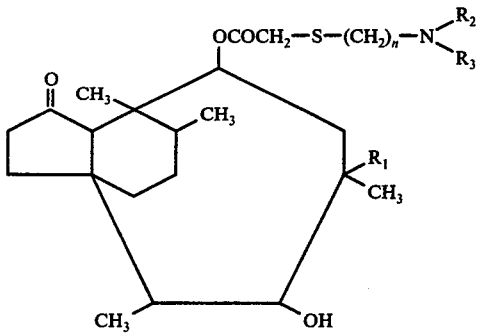

in which n is 2, 3, 4 or 5, $R_1$ is ethyl or vinyl, and either $R_2$ and $R_3$ are the same or different and each signifies alkyl of 1 to 4 carbon atoms, or $R_2$ and $R_3$, together with the nitrogen atom to which they are attached, form a heterocyclic ring optionally containing a second hetero moiety selected from oxygen, sulphur or =N—$R_5$, in which $R_5$ is alkyl of 1 to 4 carbon atoms, or an acid addition salt form thereof, comprising reacting a compound of formula II,

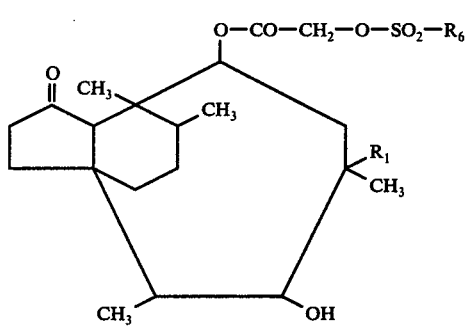

in which $R_1$ is as defined above, and $R_6$ is alkyl of 1 to 4 carbon atoms or phenyl, unsubstituted or substituted by alkyl of 1 to 4 carbon atoms, with a compound of formula III,

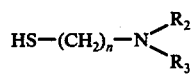

in which n, $R_2$ and $R_3$ are as defined above, characterised in that the reaction is effected in the presence of a phase transfer catalyst.

The process is suitably effected by addition of a solution of the compound of formula II in an inert, water-immiscible solvent, for example an aromatic solvent, such as toluene, to an aqueous solution of the compound of formula III, which is suitably in the form of an acid addition salt, for example in hydrochloride salt form. The reaction is conveniently effected at a temperature of from 25° to 70° C. Suitable phase transfer catalysts are conventional such catalysts, including benzyl tributylammonium bromide and tetrabutylammonium bromide. The catalyst is conveniently present in catalytic amounts, for example 1 to 2 mol %. The reaction mixture is then suitably made alkaline, for example by addition of aqueous alkali metal hydroxide, e.g. sodium hydroxide solution.

The resulting compounds of formula I may be isolated and purified in conventional manner. Where required, free base forms thereof may be converted into acid addition salt forms in conventional manner, and vice versa. Suitable salt forms include the hydrochloride and hydrogen fumarate.

The compounds of formula II are known and may be produced by reacting a compound of formula IV,

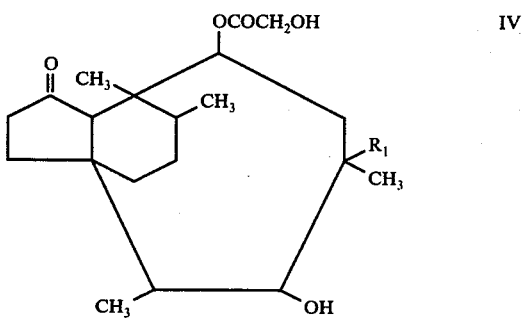

in which $R_1$ is as defined above, with a compound of formula V,

in which A is the acid radical of a reactive ester.

The reaction may be effected in known manner, for example as described in Example 1 hereinafter. "A" suitably signifies chlorine or bromine. The resulting compounds of formula II may, if desired, be isolated and purified using conventional techniques but are preferably employed without isolation in the subsequent step of producing compounds I.

The compounds of formula I are known antibiotics with anti-bacterial activity and may, for example, be used for treating (prophylaxis or therapy) microorganism infections in domestic animals, e.g. pigs and poultry.

The preferred compounds of formula I are those in which n is 2 or 3, in particular 2. $R_1$ may be ethyl but is preferably vinyl. $R_2$ and $R_3$ are preferably each alkyl of 1 to 4, in particular 1 to 3, carbon atoms, more particularly 2 carbon atoms. They may, however, as indicated, also form a heterocyclic ring together with the nitrogen atom to which they are attached. Such ring suitably contains a second hetero moiety. When the ring contains 6 ring members, this is preferably para to the nitrogen atom. The second hetero moiety is preferably oxygen or, more preferably, =N—$R_5$. $R_5$ is preferably alkyl of 1 to 2 carbon atoms.

The process of the invention is generally known. It has, however, been found that by carrying out the process in the presence of a phase transfer catalyst, not only are the yields improved somewhat but also the need to isolate the starting material of formula II can be eliminated. In addition, the process may be effected in solvents such as toluene, which may more easily and completely be regenerated thus leading to decreased environmental problems. Finally, the required reaction time is diminished and working up is simplified.

The following Examples illustrate the invention.

EXAMPLE 1:

14-Desoxy-14-[(2-diethylaminoethyl)mercaptoacetoxy]mutilin 250 g of 14-desoxy-14-hydroxyacetoxymutilin are suspended in a mixture of 900 ml of toluene and 300 ml of 15% aqueous sodium hydroxide solution, at room temperature. The mixture is heated to about 60° C and mixed, with stirring, with a solution of 138 g of p-toluenesulphonyl chloride in 350 ml of toluene. The mixture is stirred for 1½ hours at 60° C and the still warm aqueous phase is separated off. The toluene phase containing 14-desoxy-14-tosyloxyacetoxymutilin is mixed with 112 g of diethylaminoethanethiol hydrochloride, 175 ml of water and 3.5 g of benzyltributylammonium bromide and 165 ml of concentrated caustic soda are added, with stirring to the resulting mixture at 60° C. The mixture is stirred for 2 hours at 60° C, the aqueous phase is then separated off and the toluene phase is extracted with dilute sulphuric acid. The $H_2SO_4$ extract is made alkaline (pH = 12) with 2N caustic soda and precipitated heading compound extracted with toluene. The toluene solution is evaporated to obtain the heading compound in the form of a yellow oil.

The resulting free base may be treated with fumaric acid in known manner to obtain the hydrogen fumarate salt form, m.p. 148°–149° C.

EXAMPLE 2:

In manner analogous to Example 1 and employing appropriate starting materials in approximately equivalent amounts, the following compounds may be obtained:

14-desoxy-14-[(2-morpholinoethyl)mercaptoacetoxy]mutilin hydrochloride, 14-desoxy-14-[(2-diisopropylaminoethyl)mercaptoacetoxy]-mutilin hydrochloride, 14-deosoxy-14-[(di-n-butylaminoethyl)mercaptoacetoxy]-mutilin hydrochloride, 14-desoxy-14-{[2-(4-methyl)piperazinoethyl)mercaptoacetoxy]}mutilin dihydrochloride, m.p. 185°–188° C, 14-desoxy-14-[(2-dimethylaminoethyl)mercaptoacetoxy]-dihydromutilin, trimethyl ammonium iodide, softening point 123°–128° C, 14-desoxy-14-[3-(di-n-butylaminopropyl)mercaptoacetoxy]-mutilin hydrochloride, softening point 45–48° C, 14-desoxy-14-[3-(di-n-butylaminopropyl)mercaptoacetoxy]-dihydromutilin hydrochloride, softening point ~90° C, 14-desoxy-14-[(2-thiomorpholinoethyl)mercaptoacetoxy]-mutilin, softening point 120°–125° C, and 14-desoxy-14-{[2-(4-methylpiperazino)ethylmercaptoacetoxy]}-dihydromutilin, dihydrochloride m.p. 220°–225° C.

EXAMPLE 3:

The procedure of Examples 1 and 2 may be effected in analogous manner but employing tetrabutylammonium bromide in place of tributylammonium bromide, in an approximately equivalent amount, to obtain the compounds indicated.

What is claimed is:

1. A process for the production of compounds of formula I,

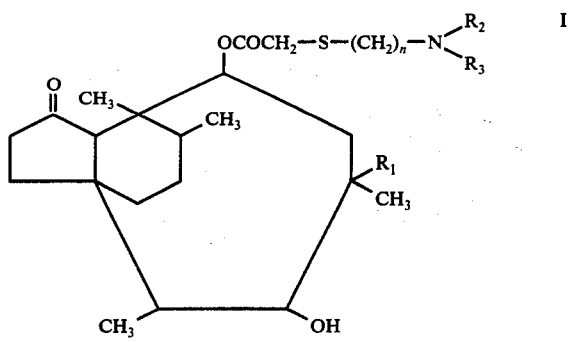

in which n is 2, 3, 4 or 5, $R_1$ is ethyl or vinyl, and either $R_2$ and $R_3$ are the same or different and each signifies alkyl of 1 to 4 carbon atoms, or $R_2$ or $R_3$, together with the nitrogen atom to which they are attached, is morpholino, thiomorpholino

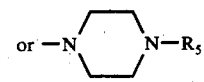

where $R_5$ is methyl or ethyl, comprising reacting a compound of formula II,

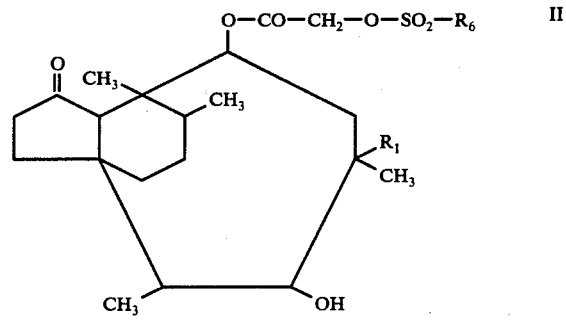

in which $R_1$ is as defined above, and $R_6$ is alkyl of 1 to 4 carbon atoms or phenyl, unsubstituted or substituted by alkyl of 1 to 4 carbon atoms, with a compound of formula III,

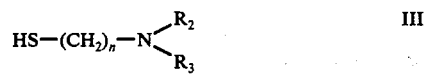

in which n, $R_2$ and $R_3$ are as defined above, characterized in that the reaction is effected under alkaline conditions in the presence of a phase transfer catalyst.

2. A process according to claim 1, in which the phase transfer catalyst is benzyltributylammonium bromide or tetrabutylammonium bromide.

3. A process according to claim 1, in which the reaction is effected by mixing a solution of the compound of formula II, in an inert, water-immiscible organic solvent with an aqueous solution of the compound of formula III or mixture of the compound of formula III with water.

4. A process according to claim 3, in which the inert water-immiscible organic solvent is toluene.

5. A process according to claims 1 in which the compound of formula I is isolated in the form of an acid addition salt by treating the compound of formula I with a salt forming organic or inorganic acid.

6. A process according to claim 5 in which the salt forming acid is hydrochloric acid or hydrogen fumarate.

7. A process according to claim 1, in which a compound of formula IV,

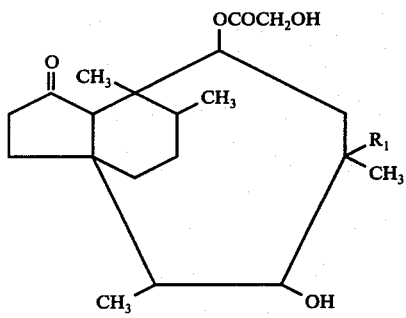    IV in which $R_1$ is as defined in claim 1, is reacted in a water immiscible solvent with a compound of formula V, $$R_6SO_2A \qquad \qquad V$$

in which $R_6$ is as defined in claim 1 and
A is the acid radical of a reactive ester, to form a compound of formula II,

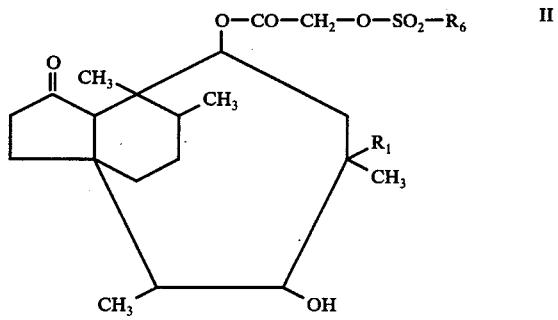    II in solution in the water immiscible solvent and thereafter reacting, in the presence of a phase transfer catalyst, the water immiscible solution of the compound of formula II with an alkaline aqueous solution of a compound of formula III,

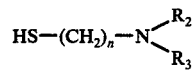    III in which n, $R_2$ and $R_3$ are as defined in claim 1.

* * * * *